United States Patent [19]

McRae

[11] Plant 4,334

[45] Nov. 21, 1978

[54] LILY PLANT: LILIUM PEACHBLUSH

[75] Inventor: Edward A. McRae, Boring, Oreg.

[73] Assignee: Melridge, Inc., Sandy, Oreg.

[21] Appl. No.: 865,013

[22] Filed: Dec. 27, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Eugene D. Farley

[57] ABSTRACT

A new variety of Asiatic hybrid lily plant, bearing large clusters of unusually large flowers of excellent form, unusual color and long persistence, both on the plant and as cut flowers. The flowers of the new plant are particularly characterized by their peach-pink color tone which is completely new in the upright and outfacing Asiatic divisions of lilies. The plant is highly resistant to disease and shows high resistance to virus. It is an excellent garden plant. The bulbs may be precooled and forced for cut flowers. The clone is very vigorous and is an excellent grower and propagator.

2 Drawing Figures

BACKGROUND OF THE INVENTION

My new variety of lily plant originated as a seedling selected from a group of seedlings at Gresham, Oreg. The seedlings were planted during a breeding program carried on by me since the year 1965. This program had as its primary objective the production of upright hybrid Asiatic lilies in the pink and peach shades, characterized by plant vigor, rapid propagation, high resistance to disease, tolerance of infection by virus, having flowers of superior form and color, and suitable for producing cut flowers when forced from pre-cooled bulbs.

I achieved the desired objective by using as the seed parent a clone selected from crossing Lilium × 'Cinnabar' with a lilac-colored seedling from the complex hybrid Lilium 'Harlequin' strain. The pollen parent was produced from crossing an unspotted clone of *Lilium dauricum* with a clone from the complex hybrid Lilium 'Hallmark' strain.

My new lily plant has vigorous growth and propagation characteristics. Its stems are dark in color and provide an attractive contrast to the abundant foliage which is deep green in color with a reddish cast.

The plant has a large number of buds, producing from 7 to 12 from a bulb 5 to 7 inches in circumference. The buds are a unique and attractive peach-pink color when the tepals first divide, and this color intensifies when the tepals begin to unfurl.

The flowers are particularly distinctive. They are characterized by tepals of fine form, unusual breadth and thickness, and sharp clean outline. They are lightly spotted, primarily at the base, and are an unusual and unique peach-pink color, with a deeper gold flush at the center and with a deeper pink flush at the tepal tips.

The plant is one of the most vigorous upright Asiatic lilies yet produced. It is a rapid propagator, and has superb disease resistance and a high degree of tolerance to infection by virus. It is an excellent garden lily and satisfactory for use in the cut flower or pot plant trade by forcing precooled bulbs, all as observed at Gresham, Oreg.

My new variety of lily plant has been asexually reproduced by me and under my direction at Gresham, Oreg. Successive generations produced by bulb scale propagation and natural propagation from bulblets have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing which shows the plant, its stem and foliage, its buds in their various stages of development, and the open bloom in full color. Also shown is the tepal arrangement, the great width of the tepals, the connection of the flower to the stalk, and particularly the unique peach-pink color of the flower.

DESCRIPTION OF THE NEW VARIETY

The following is a detailed description of my new variety of Asiatic hybrid lily, with nomenclature according to *The International Lily Register* (Royal Horticultural Society, London, 2nd edition, 1969) and with color designations according to the Royal Horticultural Society Color Chart, published by the Royal Horticultural Society in 1966.

THE PLANT

Origin: Seedling.

Parentage:

*Seed parent.*—Lilium × 'Cinnabar' (unpatented) × a lilac-colored clone from the complex hybrid Lilium 'Harlequin' strain.

*Pollen parent.*—An unspotted clone of *Lilium dauricum* × a clone from the complex hybrid Lilium 'Hallmark' strain.

Classification:

*Botanic.*—Hybrid Lilium cultivar; Division I-A of the Horticultural Classification of Lilies of the R.H.S.

*Commercial.*—Asiatic hybrid lily.

Form: Single stem, tall and stately.

Height: 20 to 30 inches from bulbs of 5 to 7 inch circumference.

Growth: Very vigorous and upright with exceptional strength.

Foliage:

*Quantity.*—Abundant.

*Size of leaf.*—3 to 4 inches long.

*Shape of leaf.*—Lanceolate.

*Texture.*—Leathery and glossy.

*Color.*—Deep green with reddish cast on both upper and under sides.

Bulbs:

*Size.*—Any size, ranging up to about 12 inches in circumference.

*Color.*—Pure white.

THE BUD

Form: Obtuse; urn-shaped.

Size: 3 to 4 inches long and 1 to 2 inches in circumference just prior to opening.

Opening: Bud opens slowly.

Color: Soft peach-pink when tepals first divide. The peach-pink color intensifies when the tepals begin to unfurl.

Tepals: The tepals curl back. They are soft peach-pink on the outerside; inside they are peach-peach with deeper gold flush at the throat and deeper pink flush at the tepal tips.

Peduncle: 2 to 4 inches long; erect, deep green in color.

THE FLOWER

Blooming habit: Recurrent. Annually in June-July. Blooms once and profusely.

Size: Large; 6–7 inches in diameter.

Borne: In clusters, from 7 to 12 on a single stem, from a bulb 5 to 7 inches in circumference.

Shape: Cup shaped, without substantial change in form with age. The tepals reflex back slightly as the bloom matures.

Tepalage:

*Number of tepals.*—6.

*Arrangement.*—Imbricated.

*Color.*—The outerside of the tepals are RHS 35 D. The inner tepals have a throat of RHS 26 B-C blending to RHS 29 C-D in the center, blending into RHS 48 C-D at the tips. The tips lighten to RHS 35 D as the flower ages.

*Tepal longevity.*—Tepals stay on the stem about 3 weeks.

*Spotting.*—Lightly spotted with small spots at the base of the tepals.

Pedicel:

*Length.*—About 2 to 4 inches.

*Color.*—Deep green.

*Form.*—Sturdy and upright.

Color change: The peach-pink of the flower changes to slightly more golden apricot-pink as the flower ages.

Appearance: The flower is shiny.

Disease resistance: The flower and plant are highly resistant to disease; in particular, they are resistant to Fusarium and Botrytis.

Fragrance: The flower is not fragrant.

Lasting quality: The flower is long lasting on the plant and exceptionally long lasting as a cut flower.

THE REPRODUCTIVE ORGANS

Stamens, anthers:

*Arrangement.*—Typical of Liliaceae.

*Length.*—About 2 inches.

*Number.*—6.

*Filaments.*—Length, about 2 inches; color, cream and reddish at tip.

Pollen and anthers: Dark reddish-brown in color.

Pistils: One in number with a length of about 2 inches.

Stigma: Deepest purple in color.

Characteristics of ovaries: Typical of genus Lilium.

THE FRUIT

Fertility: The fruit is fertile.

Shape: The fruit is ovoid.

Color at maturity: The fruit is soft brown.

My new variety of Asiatic hybrid lily most nearly resembles the variety 'Sunrise' (unpatented) but is distinguished therefrom by its peach-pink color, exceptionally broad-tepalled flowers, and upright flowers.

I claim:

1. A new and distinctive variety of Asiatic hybrid lily plant substantially as herein shown and described, characterized by its stately and erect growth; the great vigor of its growth; its strong stem; its abundant deep green foliage; its numerous buds, colored peach-pink when the tepals first divide and unfurl; the fine form and texture of the flowers; the exceptionally broad tepals; its rapid propagation characteristics; its superb disease resistance; its high tolerance to virus; its versatility both as a garden flower and as a cut flower produced by forcing precooled bulbs; and in particular its peach-pink color tone which is unique in the hybrid Asiatic division of upright lilies suited to forcing.

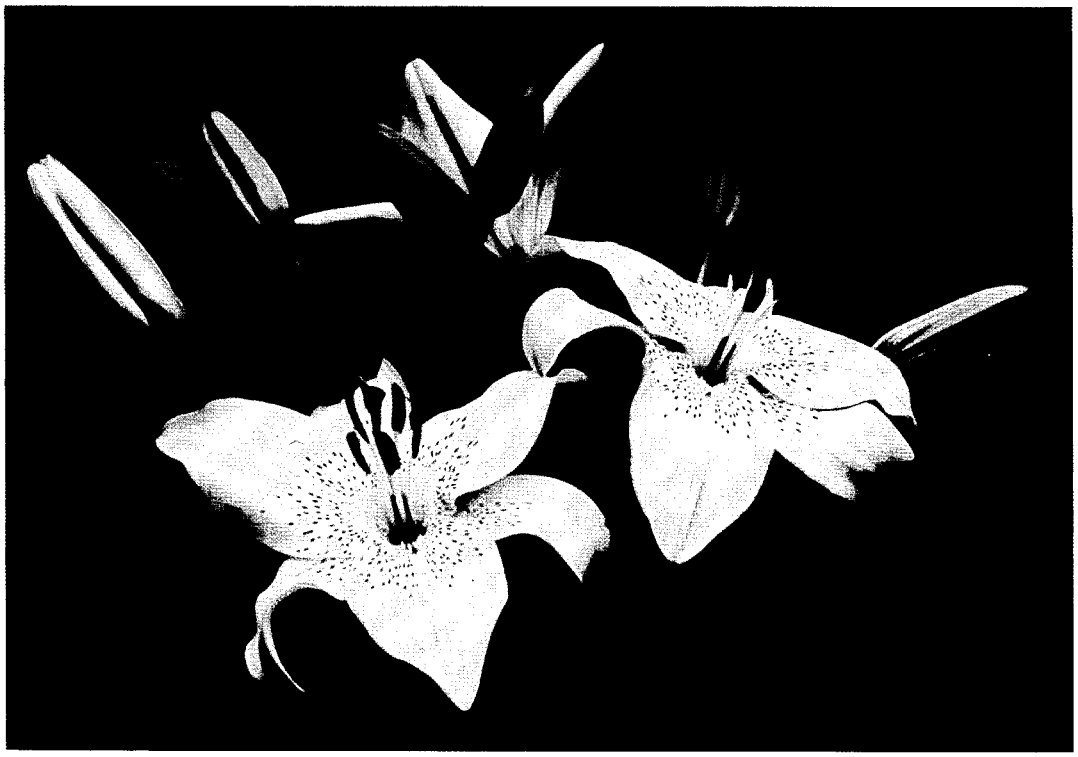

* * * * *